United States Patent [19]

Ponder

[11] Patent Number: 5,539,934
[45] Date of Patent: Jul. 30, 1996

[54] PROTECTIVE HELMET COOLING APPARATUS

[76] Inventor: Christopher W. Ponder, 788 New Hope Rd., Fayetteville, Ga. 30214

[21] Appl. No.: 371,475

[22] Filed: Jan. 11, 1995

Related U.S. Application Data

[63] Continuation of Ser. No. 157,903, Nov. 24, 1993, abandoned.

[51] Int. Cl.$^6$ ............................................. A42B 3/10
[52] U.S. Cl. ........................... 2/413; 2/414; 2/422; 2/425
[58] Field of Search ................................. 2/410, 411, 413, 2/414, 422, 424, 425, 171.2, 171.3; 607/108, 109, 110, 111, 112; 62/4; 252/70, 71; 106/13

[56] References Cited

U.S. PATENT DOCUMENTS

| | | | |
|---|---|---|---|
| 3,032,772 | 5/1962 | Fonash | 2/2.1 |
| 3,804,077 | 4/1974 | Williams | 126/263 |
| 4,133,055 | 1/1979 | Zebuhr | 2/411 |
| 4,172,495 | 10/1979 | Zebuhr et al. | 2/413 |
| 4,370,754 | 2/1983 | Donzis | 2/413 |
| 4,551,858 | 11/1985 | Pasternack | 2/7 |
| 4,573,447 | 3/1986 | Thrash et al. | 252/70 |
| 4,627,114 | 12/1986 | Mitchell | 2/414 |
| 4,780,117 | 10/1988 | Lahey et al. | 62/4 |
| 4,853,980 | 8/1989 | Zarotti | 2/413 |
| 4,964,402 | 10/1990 | Grim et al. | 128/804 |
| 5,106,520 | 4/1992 | Salyer | 252/70 |
| 5,339,796 | 8/1994 | Manker | 252/70 |

FOREIGN PATENT DOCUMENTS

| | | | |
|---|---|---|---|
| 2166373 | 6/1990 | Japan | 62/4 |

*Primary Examiner*—Michael A. Neas
*Attorney, Agent, or Firm*—Kenneth S. Watkins, Jr.

[57] ABSTRACT

An improved cooling apparatus for a protective helmet is disclosed. The cooling apparatus employs hook and loop fastener strips to secure the bladder to the helmet padding. The bladder is filled with a breakable pouch of encapsulated ammonium salt surrounded by water. An annular chamber in the bladder allows free communication of the cooling medium within the chamber to allow for differnet heat loads at different areas of the bladder.

1 Claim, 2 Drawing Sheets

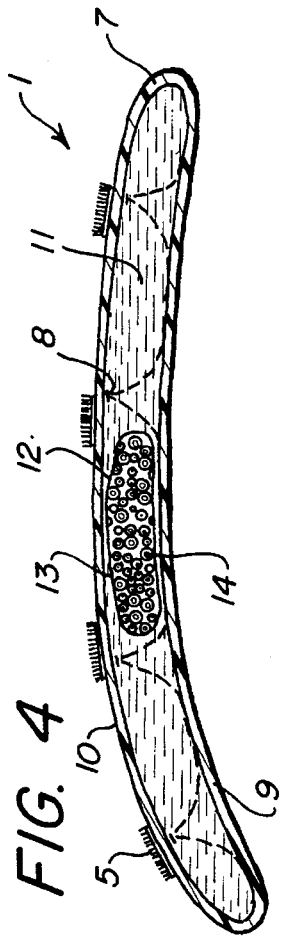
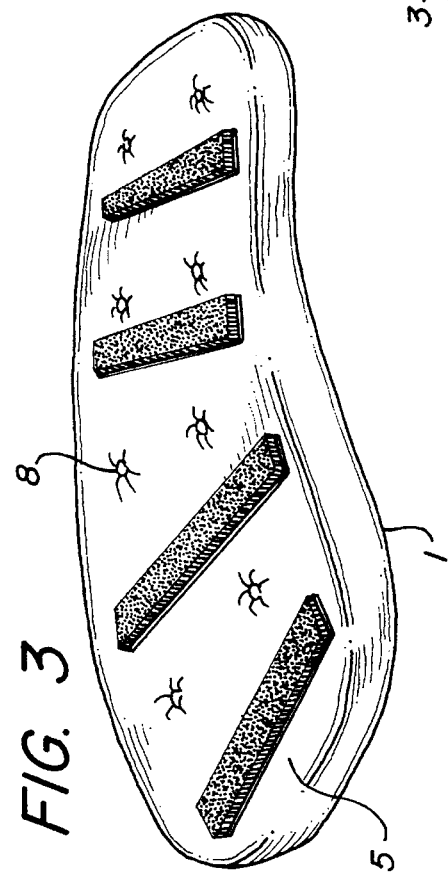
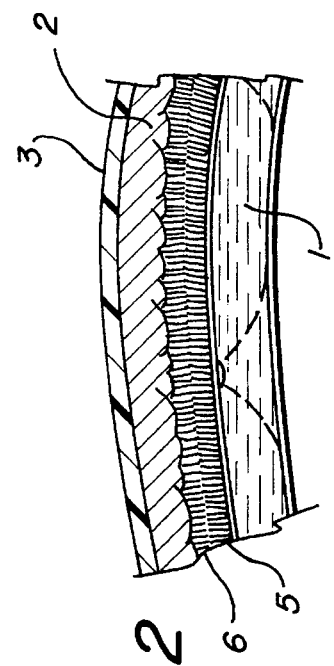
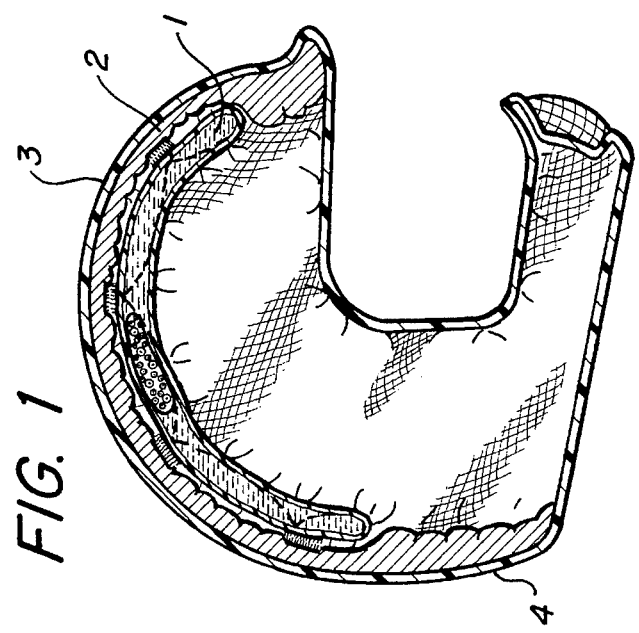
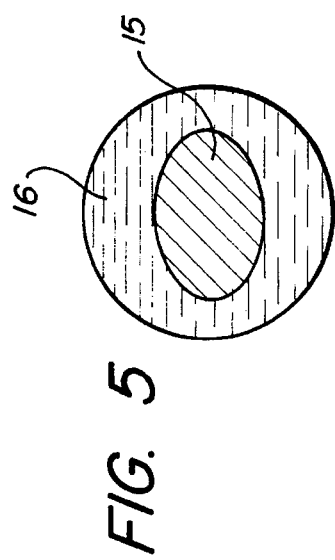

PROTECTIVE HELMET COOLING APPARATUS

This is a continuation of application Ser. No. 08/157,903 filed Nov. 24, 1993, now abandoned.

The invention relates to an easy-to-remove cooling apparatus for a protective helmet.

Protection of the head is important in many sports and hazardous work situations. Although mechanical protection of the head is often satisfactory, the user may become uncomfortable due to the heat retentive aspects of the protective head gear. For example, motorcycle racers usually race in the hot summer months and are subjected to extreme heat conditions. Dirt bike racers in motocross do not attain significant speeds to allow sufficient air flow through the helmet. Extremely high temperatures inside the helmet can impair judgment, reduce concentration, and even cause visual problems.

In the past, helmets have been introduced with various methods to increase air circulation inside the helmet. Most of these are ineffective if air movement across the helmet is low, or in high ambient temperature environments. The addition of devices such as blowers or air chilling equipment results in additional weight, bulk, and expense.

Cooling bladders have been used in the past, but, until now, the bladders have been difficult to replace quickly and refilling of the bladders is time-consuming and messy. In addition, wall and seam construction of these bladders has restricted communication of the cooling medium in the bladder to areas of different heat load.

The Protective Helmet Having a Cooling Harness (U.S. Pat. No. 4,551,858) includes a cooling bladder which is buttoned inside the helmet by use of a harness. After a period of contact with the user's head, the coolant may become warm and would, therefore, offer no cooling effect. The bladder is cumbersome to replace or refill when the coolant becomes too warm to be effective.

Users such as motorcycle racers, firemen, auto racers, and others who must wear protective helmets for extended periods of time require a cooling means which remains effective for long periods of time and a system whereby the cooling means can be easily and quickly replaced when it becomes ineffective.

My invention consists of a cooling bladder which fits into a protective helmet and is restrained with hook and loop fastener strips within the padded interior area of the helmet so the bladder is in contact with the user's head.

The bladder can be easily replaced by pulling out the old bladder and pressing another bladder into place so the hook and loop fastener strips are in contact with the hook and loop fastener strips inside the protective helmet. The concave inside wall and the concave outside wall of the bladder are connected by bonded attachment points which maintain an annular chamber of arcular shape and allow the cooling medium within the chamber to communicate freely without restriction throughout the chamber.

The bladder is filled with water and contains a pouch of ammonium salt such as ammonium nitrate. Mixing the water and ammonium salt by breaking the pouch results is a cooling effect to the wearer. Because the ammonium salt is encased in a water-soluble coating, the dissolving rate of the ammonium salt is controlled and the chilling effects of the bladder are extended.

My protective helmet cooling apparatus provides cooling effects over extended periods of time and the bladder is quick and easy to remove and replace with another cooling bladder.

DESCRIPTION OF DRAWINGS

These and other features, aspects, and advantages of the present invention will become better understood with regard to the following description, appended claims, and accompanying drawings where:

FIG. 1 shows cross-section of helmet cooling apparatus;

FIG. 2 shows a detail of FIG. 1;

FIG. 3 shows perspective view of cooling bladder;

FIG. 4 shows cross-section of cooling bladder; and

FIG. 5 shows cross-section of ammonium salt capsules.

DESCRIPTION

Figure 6:
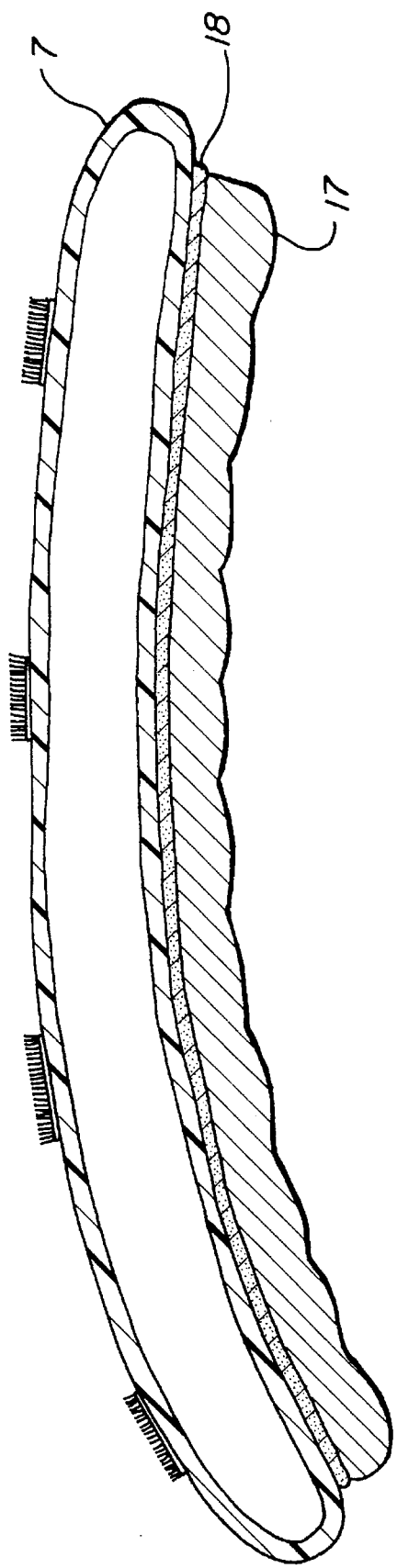
FIG. 6 is a cross-section of the bladder with a fabric pad.

FIG. 1 shows a cross-section of the helmet cooling apparatus. A hermetically sealed cooling bladder 1 fits in a recessed area of the helmet padding 2. The padding is bonded to the inside of outer shell 3 of the helmet 4.

FIG. 2 shows a method of bladder attachment. Hook and loop fastener such as VELCRO strip 5 which is bonded to bladder 1 attaches to matching hook and loop fasteners strip 6 which in turn is fastened to padding 2. FIG. 3 shows one arrangement of hook and loop fasteners strips 5 on bladder 1.

FIG. 4 is a cross-section of bladder 1 showing bladder wall 7 which is a flexible, durable material such as rubber or plastic, and is made up of a concave side 9 and an convex side 10. Attachment points 8 bond sections of convex side 10 and concave side 9 to form an annular chamber 11 of arcular shape as shown in FIG. 4. This results in a quilted effect as shown in FIG. 3. When installed in the recessed padded area, the convex side 10 conforms to the curvature of the recessed area of the helmet padding, and concave side 9 conforms to the curvature of the head of the user. The annular chamber 11 is filled with water and contains pouch 12 which is made of a thin, waterproof membrane 13. This membrane is capable of being ruptured or broken when deformed by an external force such as pressing or squeezing by the fingers of one's hand through the bladder wall 7. The pouch 12 is filled with capsules 14.

A cross-section of the capsules is shown in FIG. 5. An ammonium salt 15 such as ammonium nitrate or ammonium chloride which is capable of producing an endothermic reaction when dissolved in water is encased in a water-soluble cover 16, which may be gelatin. The thickness and/or composition of the water-soluble cover may be selected to provide the desired dissolving time of the coating. In practice, capsules with several different coatings may be enclosed in the pouch to result in a cooling effect over the desired time range.

FIG. 6 shows an alternative embodiment of bladder 1. A fabric pad 17 is fastened to the concave side of wall 7 utilizing a fastening means such as bonding 18. The fabric pad improves the comfort to the user.

The use of attachment points 8 between concave side 9 and convex side 10 of bladder wall 7 maintains an annular chamber 11 of arcular shape in which the cooling medium can communicate freely within the chamber. This communication allows continued cooling effect despite differences in the cooling load at different locations adjacent to the bladder.

It is recognized that various modifications are possible. The number and shape of the bladders may be changed to produce the desired effect in different helmet designs. The bladder may have a fill means and a sealing means to allow re-use of the bladder by enabling the addition of water and ammonium salt capsules and removal of the dissolved mixture after use.

I claim:

1. A motorcycle helmet cooling apparatus comprising:

a protective helmet shell;

a helmet padding bonded to an inside portion of the protective shell, the padding comprising a recessed portion; and a bladder made of a flexible material and comprising a convex side and a concave side, the convex side and the concave side bonded by a plurality of attachments points in a quilted fashion to form an annular chamber, the annular chamber of the bladder further comprising water, at least one capsule and a waterproof membrane, said at least one capsule comprising a salt capable of producing an endothermic reaction with the water and a water soluble coating encapsulating the salt and thereby extending a cooling effect, and wherein the waterproof membrane separates said at least one capsule from the water, the waterproof membrane capable of being ruptured by an external force such as pressing by fingers of a hand, the bladder being retained in the recessed area of the helmet padding by a hook and loop fastener.

* * * * *